United States Patent [19]

Poltera

[11] Patent Number: 5,637,594
[45] Date of Patent: Jun. 10, 1997

[54] ANTIMALARIAL SYNERGISTIC COMPOSITIONS CONTAINING BENFLUMETOL

[75] Inventor: Anton A. Poltera, Allschwil, Switzerland

[73] Assignee: Ciba Geigy Corporation, Tarrytown, N.Y.

[21] Appl. No.: 476,175

[22] Filed: Jun. 7, 1995

Related U.S. Application Data

[63] Continuation of Ser. No. 129,103, filed as PCT/EP93/00163, Jan. 25, 1993, abandoned.

[30] Foreign Application Priority Data

Apr. 11, 1991 [DE] Germany ............... 91810271.6
Feb. 7, 1992 [DE] Germany ............... 92810089.0
Feb. 21, 1992 [DE] Germany ............... 92810130.2

[51] Int. Cl.$^6$ ............... A61K 31/44; A61K 31/47; A61K 31/135
[52] U.S. Cl. ............... 514/292; 514/313; 514/653
[58] Field of Search ............... 514/653, 305, 514/292, 313

[56] References Cited

U.S. PATENT DOCUMENTS 5,219,865  6/1993  Chatterjee et al. ............... 514/305

FOREIGN PATENT DOCUMENTS 0362810  4/1990  European Pat. Off. .
9202217  2/1992  WIPO .

OTHER PUBLICATIONS

Chem Abs. 112(7): 48094s of R. Deng. Recent Progress in Research on Antimalarial in China, Zhongguo Yiva Gongye Zazhi, 20(8), 372–6 (1989).

The Merck Index 11th Edition, Merck & Co Rahway, NJ 1989, p. 1283.

Primary Examiner—Jerome D. Goldberg
Attorney, Agent, or Firm—Marla J. Mathias

[57] ABSTRACT

The invention relates to a synergistic antimalarial composition which comprises the antimalarial agent benflumetol and also an antimalarial agent from the quinine group such as quinine. The composition can be formulated into solid dosage forms such as tablets and is useful for the treatment of drug resistant malaria.

3 Claims, No Drawings

ANTIMALARIAL SYNERGISTIC COMPOSITIONS CONTAINING BENFLUMETOL

This is a continuation of application Ser. No. 08/129,103 filed Sep. 30, 1993, now abandoned, which is a national stage of PCT/EP 93/00163, filed Jan. 25,1993.

The present invention relates to a synergistic antimalarial composition, methods of treating malaria by administering that composition, and to a process for the preparation of that synergistic antimalarial composition.

Drug resistant malaria is a serious clinical and public health problem. The malaria parasite *Plasmodium falciparum* has developed the versatility of evading the effects of standard drugs such as chloroquine either by genetic mutation or by non-genetic adaption method. The spread of *Plasmodium falciparum* resistant to chloroquine and other antimalarial drugs is a major challenge to health care programms in tropical and subtropical countries. Therefore, novel pharmaceutical compositions which diminish the resistance against malarial parasites, are needed for successful therapy.

The antimalarial effect of compositions containing the agent benflumetol has been reported in Chemical Abstracts 97:28538 h and 101: 136941u. Other compositions contain combinations of known antimalarial agents. For example, the combination of amodiaquine and tetracycline have been used in the clinic [Suphat Noeypatimanond, et al. (1983), Treatment of Plasmodium falciparum malaria with a combination of amodiaquine and tetracycline in central Thailand, Trans. R. Soc. Trop. Med. and Hyg. 73 (3), 338–340]. Mother antimalarial combination (FANSIMED, mefloquine, pyrimethamine and sulphadoxine) has been launched on the market [Tropical Diseases Research, Seventh Programme Report, Chapter 2; Malaria, UNDP World Bank/WHO. Published by WHO, 1985].

The use of combinations of artemisinine, its derivatives and other antimalarial compounds, such as quinine, has been published in the German Patent Application P 37 15 378. Also the synergistic effect of a combination of artemisinine and primaquine is known (Wan Yaode, Cang Qizhong, Pharmacy Bulletin, Vol. 16, No. 1, 1981).

Combinations of the antimalarial agents artemether, arteether, artemisinine, dihydro-artemisinine, or artesunate with quinidine or with mefloquine have been disclosed in the Motivation for the present invention has been drawn from the need in therapy for an improved antimalarial composition of higher activity and lower resistance against malarial parasites such as *Plasmodium falciparum*.

It has now been found that pharmaceutical compositions containing the agent benflumetol in combination with the agent quinine or a derivative thereof have improved antimalarial activity and are more active than compositions containing only the individual component benflumetol, or alternatively, quinine derivatives.

The following invention relates to a pharmaceutical composition suitable for synergistic action of the active components against malaria comprising a synergistically effective amount of a compound of the formula:

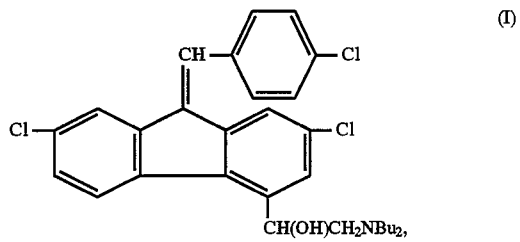

combined with a synergistically effective amount of at least one compound selected from the group (II) consisting of quinine, mefloquine, halofantrine, chloroquine, primaquine and pyronaridine or a pharmaceutically acceptable salt or derivative thereof having antimalarial efficacy.

The general definitions and terms used in this specification of the invention preferably have the following meanings:

The term pharmaceutical composition defines a mixture comprising the combination of a compound of the formula I with at least one compound of the group (II). This mixture either consists of a dry preparation of the active components (I) and (II) such as a lyophilisate or preferably contains additives suitable for the manufacture of a dosage form such as tablets, capsules or suppositories.

The term synergistic action defines the increase of efficacy of the composition above the efficacy level of at least one individual active component (I) or (II) at the given dose. Preferably, the efficacy of all active components present in the pharmaceutical composition is increased. The synergistic effect is most desirable as it enables the use of a lower dosage of an individual component and/or improvement of activity above the activity levels of the individual components.

The synergism of the claimed composition is proved by experimental results from in-vitro and in-vivo models. The results show that the activity of the component according to formula I is raised as compared to the activity of benflumetol (I) in an individual dosage form and that the activity of the component (II) is also being raised.

Synergistic action against malaria of the composition according to the present invention permits the combined application of different drug regimens during therapy by the administration of one dosage form such as one or two tablets per day.

The application of a dosage form comprising the active component benflumetol (I) allows permanent action against malaria. This is evident from tests carried out in different standard in-vitro and in-vivo pharmacological models. The presence in the same dosage form of the second active component (II) allows immediate and fast action against protozoa after the outbreak of the disease.

The active component (I) mentioned above, wherein Bu denotes n-butyl, is known under the name benflumetol, see C.A.R.N. 82186-77-4. Pharmaceutical compositions containing benflumetol individually and their activity against malaria are also known, see the abstracts according to C.A. 97:28538h and 101:136941. The preparation of benflumetol has been disclosed in the Published Chinese Patent Application 88/076666.X.

The active components selected from the group (II) consisting of quinine, mefloquine, halofantrine, primaquine and pyronaridine are known active agents useful in malaria therapy.

A pharmaceutically acceptable salt of quinine is, for example, the acid addition salt with one or two equivalents of a monobasic inorganic or organic acid or the acid addition salt with a dibasic inorganic or organic acid. Such acid addition salt is, for example, the hydrohalide salt, e.g. the hydrochloride, hydrobromide or hydroiodide salt, the dihydrohalide salt. e.g. the dihydrochloride, dihydrobromide, or dihydroiodide salt, the hydrogensulfate or sulfate salt, the hydrogencarbonate or carbonate salt, the ethylcarbonate, formate, acetate, gluconate or tannate salt of quinine.

A pharmaceutically acceptable derivate of quinine is, for example, the structurally related quinidine, cinchonine or cinchonidine derivative thereof. Those derivatives are preferably present in the composition as acid addition salt, e.g. as hydrogenhalide or dihydrogenhalide salt, e.g. as hydrochloride or dihydrochloride.

Quinine and the above-mentioned salts and derivatives thereof are known antimalarial, agents. Reference is made to the Merck Index published by Merck & Co., Inc. Tenth Edition (1983), and the various entries at pages 1164–1166.

Mefloquine (CAS Reg.No. 53230-10-7) is preferably present in the composition as hydrochloride acid addition salt (CAS Reg. No. 51773-92-3). Reference is made to the entry. No. 1381 -v at page 513 of Martindale, The Extra Pharmacopoeia, Twenty-ninth Ed., The Pharmaceutical Press London 1989.

Halofantrine (CAS Reg. Nos. 69756-53-2 and 66051-63-6) is preferably present in the composition as hydrochloride acid addition salt (CAS Reg. No. 36167-63-2). Reference is made to the entry. No. 16829-p at page 512 of Martindale, The Extra Pharmacopoeia (loc.cit.).

Chloroquine, 7-chloro-4-[4-diethylamino-1-methyl-n-butylamino]-quinoline is a known antimalarial agent from the 4-aminoquinoline group and is preferably present in the composition in the form of its diphosphate or sulfate salt. Reference is made to entry No. 2163 at page 334 of the Merck Index, Eleventh Edition.

Primaquine, 8-(4-Amino-1-methyl-n-butylamino)-6-methoxy-quinoline, is a known antimalarial agent from the 8-aminoquinoline group and is represented by the following structural formula:

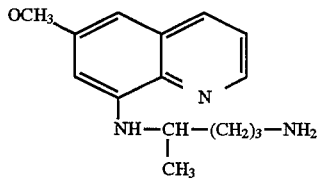

The antimalarial efficacy of this compound is also reported in Chapter 34, Parasite Chemotherapy, E. B. Roche et al., Principles of Medicinal Chemistry, W. O. Foye (Editor), Lea & Febiger, Philadelphia/London 1989.

Pyronaridine is a known antimalarial agent represented by the following structural formula:

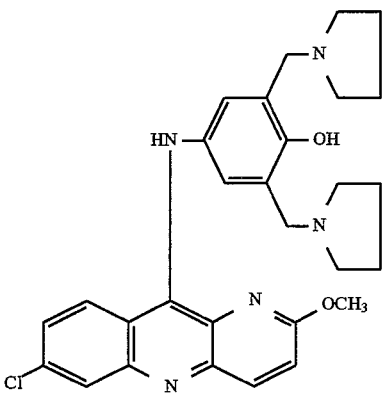

The synthesis of this compound is reported in Acta Pharmaceutica Sinica 15:630–632 (1980). The antimalarial efficacy of this compound is also reported in Practical Chemotherapy of Malaria, Report of a WHO Scientific Group, Technical Report Series 805, Geneva 1990, see Chapter 8.5, pages 122–124.

Preferred is a pharmaceutical composition suitable for synergistic action of the active components against malaria which comprises the combination of a synergistically effective amount of benflumetol (I) with a synergistically effective amount of at least one compound selected from the group (II) consisting of quinine, mefloquine and halofantrine, or a pharmaceutically acceptable salt or derivative thereof having antimalarial efficacy Especially preferred is a pharmaceutical composition suitable for synergistic action of active components against malaria which comprises the combination of a synergistically effective compound of benflumetol (I) with a synergistically effective amount of a pharmaceutically acceptable acid addition salt of quinine.

Pharmaceutically acceptable additives are preferably present in the composition according to the present invention. The additives are used for the preparation of preferably enteral or parenteral dosage forms according to conventional formulation methods.

For oral administration suitable additives include inert diluents or filers, thereby forming solid or liquid dosage forms such as tablets, powders, capsules, syrups and the like. The pharmaceutical compositions can, if desired, contain additional ingredients such as flavourings, binders, excipients and the like.

For example, tablets containing various solid additives such as starch, dextrin, alginic acid and certain complex silicates, together with binding agents such as polyvinylpyrrolidone sucrose, gelatin and acacia. Additionally, lubricating agents such as magnesium stearate, sodium lauryl sulfate and talc are often useful for tabletting purposes. Solid composition of a similar type may also be employed as fillers in soft and hard gelatin capsules, preferred materials therefore include lactose or milk sugar and high molecular weight polyethylene glycols.

For other oral dosage forms the mixture of the compounds can for example be administered in a gelatin capsule. Such formulation could be based on a suitable refined edible oil such as sunflower oil, corn oil, peanut oil, coconut oil or til oil.

In a preferred embodiment of the present invention, the active components (I) and (II) are formulated in a single unit dosage form such as tablets or capsules.

The active components (I) and (II) may also be formulated into two individual dosage forms contained within one administration system (kit of pans), which are simultaneously or consecutively administered. The same route of administration is possible, e.g. administration of two individual dosage forms contained within one kit of parts. One tablet or capsule containing component (I) and, consecutively, a second dosage form containing component (II) is administered. An individual dose regimen may be developed especially during clinical treatment, e.g. by administering after the first occurrence of malaria a tablet or capsule containing a high dose of the active component (I) or, correspondingly, multiplying lower doses in the beginning of malaria attacks, and administering also a tablet or capsule containing a lower dose of the active component (II). In the course of treatment, dosage forms containing a lower dose of component (I) and a higher dose of component (II) are administered. Different dosage forms present in one kit-of-parts may also be administered simultaneously or consecutively, e.g. by administration of a tablet containing component (I) and a suppository containing component (II). The dosage range may also be varied according to the dose regimens given above.

The usefulness of the pharmaceutical composition according to the present invention in therapy against malaria is evident from in-vitro and in-vivo results from experiments carried out in established test models. The ability of the composition to act as an effective and long-acting antimalarial agent even against strains of P.berghei known to be extremely resistant against other antimalarial agents reflects the usefulness of the present invention.

The present invention also relates to a method of treatment against malaria which comprises administering to a patient after the outbreak of malaria the above-mentioned pharmaceutical composition comprising the combined active components (I) and (II). The composition is administered to the patient for a period of time of at least four days, preferably five or more days.

The term method of treatment also comprises prophylactic administration of the composition to healthy patients to prevent the outbreak of the disease in high-risk areas of contamination, especially in regions between the tropics of capricorn and cancer.

The dose of the active component benflumetol (I) as contained in the pharmaceutical composition may vary within wide limits and depends on the condition of the patient and the time period elapsed after the outbreak of the disease. Based on in-vivo data from model experiments as reported below in the Examples, it is established that the daily dose of benflumetol is between about 0.2–50.0 mg/kg, preferably 0.2–10.0 mg/kg and especially about 0.2–5.0 mg/kg. This daily dose can be raised considerably upon need in view of low toxicity and high tolerability of benflumetol. It is also estimated that the daily dose of component (II) in the composition, is between 0.2 and 50 mg/kg, preferably 0.3–5.0 mg/kg and especially between about 0.4–3.0 mg/kg.

The dose ratio of component (I) to component (II) may also vary within wide limits. Synergism will be especially efficient if benflumetol is administered in equal weight amounts or, preferably, in excess amounts as compared to the weight amounts of component (II) administered. Accordingly, the weight amount of benflumetol may vary from one to ten parts for each part component (II), administered. Preferably, three to seven parts and especially five to six parts of benflumetol are administered for each part of component (II). The dose amounts given and dose ratios refer to daily administrations.

The invention also relates to a process for the preparation of the pharmaceutical composition suitable for synergistic action of the active components against malaria which comprises combining an effective mount of a compound of formula I with an effective amount of the component (II) and formulating this combination of active components under optional addition of pharmaceutically acceptable additives to a suitable dosage form.

The novel pharmaceutical compositions contain, for example, from 10% to 80%, preferably from 20% to 60%, of the combination of the active components. Pharmaceutical compositions according to the invention are suitable for enteral administration and are, for example, formulated into oral dosage unit forms, such as dragées, tablets, capsules or suppositories. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary, after the addition of suitable adjuncts, to form tablets or dragée cores.

In a preferred embodiment of the process, the active components (I) and (II) are milled either individually or together to particle sizes from about 10 μ to about 400 μ, preferably 20 μ to 200 μ. At least 90% of the crystals of the active components are present in the ranges.

Particles of this size are obtained by conventional comminution methods, e.g. grinding in an air jet mill, ball mill or vibrator mill. Micronisation is preferably effected by known methods using an ultrasonics disintergrator, e.g. of the Branson Sonifier type as described e.g. in J. Pharm. Sci. 53 (9), 1040–1045 (1965), or by stirring a suspension with a high-speed agitator, for example with a stirrer of the Homorex type (supplied by Brogli & Co., Basel). In these preferred methods, micronisation is effected at about 500 to 10,000 rpm (rotations per minute) by dissolving or suspending the combination of the active components in an organic solvent, e.g. methanol, ethanol or propylene glycol, and precipitating it in microcrystalline form at ca. 0°–5° C. in water or an aqueous salt solution, e.g. 2% sodium chloride solution which may additionally contain a protective colloid such as gelatin or a cellulose ether, e.g. methyl cellulose or hydroxypropyl methyl cellulose, in low concentration (0.1–1%), and filtering the resultant stirred suspension. The filter cake is dried at low temperature, e.g. ca. 0°–5° C., under vacuum (e.g. below 50 mbar, preferably at 0.5 mbar). The subsequent drying can be effected at ca. 50°–90° C.

The crystals thus obtained are then formulated to granulates, preferably by wet granulation which is carried out according to standard methods.

The pharmaceutical composition is preferably prepared by compressing a granular formulation which is obtained, for example, by sieving and, if desired, by comminuting the drug, with or without the excipients, compacting with another solvent such as ethanol or water, removing the solvent or drying, with or without the addition of lubricants or glidants such as magnesium stearate or TWEEN, comminuting the granules and sieving once more.

The granules can be compressed to tablet cores in a conventional tabletting machine, for example an EKO Korsch eccentric tabletting machine, at a pressure of ca. 10 kN. Coating can be effected by applying an aqueous-ethanolic solution in which, for example, polyethylene glycol and saccharose is dissolved or dispersed.

Dragée cores are provided with suitable coatings that may be resistant to gastric juices, there being used, inter alia, concentrated sugar solutions that may contain gum arabic, talc, polyvinylpyrrolidone or polyethylene glycol. Colorings, flavorings or pigments may be added to the syrups, tablets or dragée coatings, for example for identification purposes, masking taste or to indicate different doses of active ingredient.

Further orally administerable pharmaceutical compositions are dry-filled capsules consisting of gelatin, and also soft sealed capsules consisting of gelatin and plasticiser, such as glycerine or sorbitol. The dry-filled capsules may contain the active components in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

Suitable for enteral administration are also suppositories that consist of the combination of the active ingredients and a suppository base. Suitable as suppository bases are, for example, natural or synthetic triglycerides, paraffins, polyethylene glycols or higher alkanols. It is also possible to use gelatin rectal capsules that contain a combination of the active ingredient and a base material; suitable base materials are, for example, liquid triglycerides, polyethylene glycols or paraffin hydrocarbons.

The following Examples illustrate the invention described above; they are not, however, intended to limit the scope of the invention in any way.

EXAMPLE

Preparation of Tablets

| | |
|---|---|
| benflumetol | 120 mg |
| quinine dihydrochloride | 20 mg |
| corn starch | 100 mg |
| dextrin | 40 mg |
| Tween®-80 | 0,6 mg |
| 15% paste of corn starch | "sufficient" |
| Mg-stearate | 3 mg |

Quinine dihydrochloride crystals are passed through a 100 mesh size sieve. Benflumetol crystals are passed through a 60 mesh size sieve and mixed with the quinine solid, starch and dextrin. This mixture is passed 3 times through a 40 mesh size sieve. Tween®-80 is added to the paste of starch which is mixed with the above formulation. This mixture is granulated by way of wet-granulation, passed through a 40 mesh size sieve, dried at reduced pressure at 50°–60° C. The Mg-stearate is added, and the tablets are pressed.

I claim:

1. A pharmaceutical composition suitable for synergistic action of the combined active components against malaria, which composition comprises synergistic antimalarially effective amounts of a combination of the compound of the formula (I):

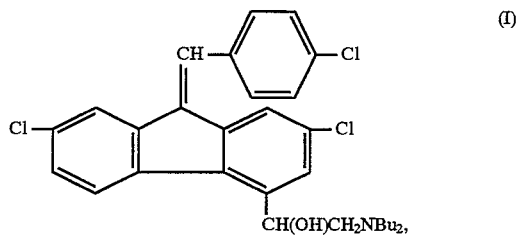

in fixed combination with at least one compound (II) selected from the group consisting of chloroquine and pyronaridine or a pharmaceutically acceptable salt having antimalarial efficacy.

2. A pharmaceutical composition according to claim 1, wherein the compound (II) is a pharmaceutically acceptable salt of chloroquine.

3. A method for treating or preventing malaria which comprises administering orally to a patient in need of such treatment a synergistic antimalarially effective amount of a pharmaceutical composition according to claim 1.

* * * * *